United States Patent [19]

Hukuba

[11] Patent Number: 4,726,806
[45] Date of Patent: Feb. 23, 1988

[54] ELECTRIC TOOTH-BRUSH

[76] Inventor: Hiroshi Hukuba, No. 914-1, Nazukari, Nagareyama-shi, Chiba-ken, Japan

[21] Appl. No.: 890,794

[22] Filed: Jul. 24, 1986

Related U.S. Application Data

[63] Continuation of Ser. No. 762,976, Aug. 6, 1985, abandoned.

[30] Foreign Application Priority Data

| Aug. 14, 1984 | [JP] | Japan | 59-169551 |
| Sep. 16, 1984 | [JP] | Japan | 59-193504 |
| Nov. 4, 1984 | [JP] | Japan | 59-232119 |
| May 5, 1985 | [JP] | Japan | 60-95745 |

[51] Int. Cl.⁴ .................. A61N 1/26; A61N 1/44
[52] U.S. Cl. .................. 604/20; 15/167.1; 128/393; 132/84 R
[58] Field of Search .......... 128/393; 15/167 R; 604/20; 132/84 R

[56] References Cited

U.S. PATENT DOCUMENTS

| 407,115 | 7/1889 | Pratt | 15/167 R X |
| 1,887,913 | 11/1932 | Bell | 15/167 R UX |
| 2,219,753 | 10/1940 | Seguin . | |
| 2,722,703 | 11/1955 | Green . | |
| 2,834,344 | 5/1958 | Kanai | 15/167 R X |
| 3,271,805 | 9/1966 | Sawyer . | |
| 3,478,741 | 11/1969 | Simor | 15/167 R X |
| 3,488,788 | 1/1970 | Robinson . | |
| 3,667,454 | 6/1972 | Prince . | |
| 4,227,276 | 10/1980 | Ginsburg et al. . | |
| 4,526,570 | 7/1985 | Nakagawa et al. | 604/20 |

FOREIGN PATENT DOCUMENTS

| 16564 | 10/1980 | European Pat. Off. . | |
| 750214 | 5/1933 | France . | |
| 1538649 | 7/1968 | France . | |
| 1558852 | 1/1969 | France . | |
| 95197 | 6/1970 | France . | |
| 2218860 | 9/1974 | France . | |
| 43-5092 | 3/1968 | Japan . | |
| 48-27390 | 8/1973 | Japan | 15/167 R |
| 58-2701 | 1/1983 | Japan . | |
| 58-41549 | 3/1983 | Japan . | |
| 202424 | 8/1923 | United Kingdom . | |
| 390985 | 4/1933 | United Kingdom . | |
| 956126 | 4/1964 | United Kingdom . | |

Primary Examiner—Anton O. Oechsle
Attorney, Agent, or Firm—Flynn, Thiel, Boutell & Tanis

[57] ABSTRACT

An electric tooth-brush has a head portion studded with bristles, and a grip portion removably coupled thereto. The grip portion accomodates a battery and carries an electrically conductive bar which has one end connected to the battery and the other end projecting outwardly from one end of the grip portion. The top surface of the grip portion is mounted with an electrically conductive cover which is connected to the battery.

15 Claims, 12 Drawing Figures

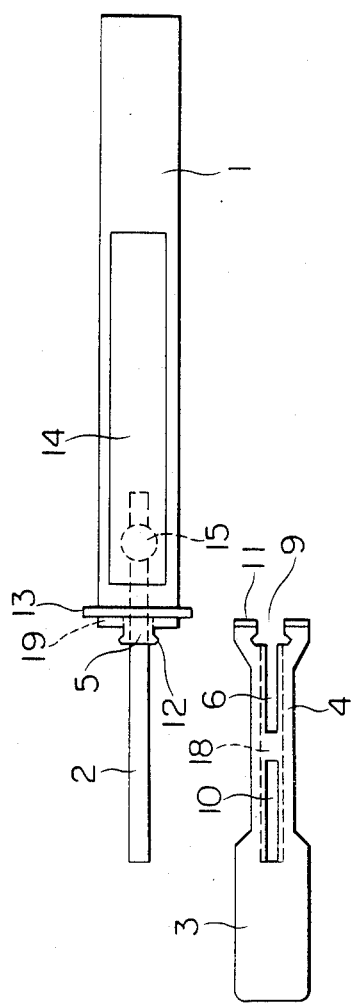
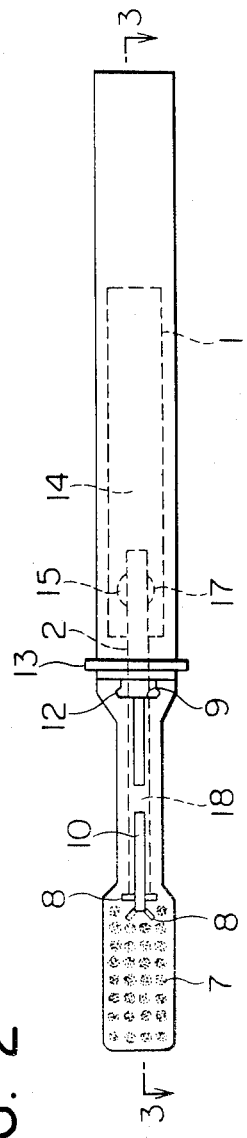
FIG. 1
FIG. 2

ELECTRIC TOOTH-BRUSH

This application is a continuation of U.S. Ser. No. 762,976, filed Aug. 6, 1985, now abandoned.

BACKGROUND OF THE INVENTION

This invention relates to an electric tooth-brush having an electric potential generating means.

A conventionally known electric tooth-brush of this type has a handle comprised of a head portion studded with bristles, and a grip portion removably coupled to the head portion. In the head portion, a head conductor member is embedded having one end exposed to the bristles and the other end exposed to one end of the head portion opposite to the bristles. The grip portion accommodates a battery and carries on its top surface a grip conductor member connected to the battery. When the grip portion is coupled to the head portion, the head conductor member is electrically connected to the battery. In use, the battery, the grip conductor member, a user body and the head conductor member constitute a closed circuit which, when a tooth paste containing fluoride is used, causes electrical permeation of fluorine ions into the teeth, thereby ensuring protection and prevention against tooth decay and pyorrhea.

Generally, after repetitions use of the tooth-brush, its bristles will be worn and torn and the tooth-brush, now being of no use, must be put in disposal. The usable term normally amounts to about one month.

When, in the conventional tooth-brush described previously, wear and tear of the bristles occurs, the head portion is put in disposal and replaced with new one but the grip portion, not subject to replacement, is put in further use. This leads to cost reduction as compared to the cost charged for disposal of the entire tooth-brush. However, the head conductor member embedded in the head portion is inseparable therefrom and therefore, upon disposal of the head portion, the head conductor member is simultaneously put in disuse even if it is still usable, resulting in a disadvantage of insufficient cost reduction. Furthermore, the head portion with the head conductor member embedded is complicated in structure.

SUMMARY OF THE INVENTION

An object of this invention is to provide an electric tooth-brush which can eliminate the drawbacks of the conventional tooth-brush by having a simplified and inexpensive head portion which can be removably coupled to a grip portion with ease but is difficult to separate from the grip portion once rigidly coupled thereto and which can be dispensed with a head conductor member.

According to this invention, the above object can be accomplished by an electric tooth-brush having a handle including a grip portion and a head portion separable therefrom, wherein the grip portion accommodates a battery and carries a head conductor member which has one end connected to the battery and the other end projecting outwardly from one end of the grip portion opposing the head portion, and a grip conductor member which covers a top surface of the grip portion and which is connected to the battery, and wherein the head portion is formed with an insertion hole in which the head conductor member is fitted and communication holes through which the insertion hole is in communication with bristles. Upon disposal of the head portion, the head portion is separated from the grip portion with the battery, head conductor member and grip conductor member retained on the side of the grip portion. This ensures disposal of the head portion alone which is inexpensive. In use, when the two portions are coupled together, electrical connection between the head conductor member and the bristles is established through liquid such as saliva which is created during tooth brushing and flows into the communication holes through which the insertion hole formed in the head portion for reception of the head conductor member is in communication with the brush threads.

Another object of this invention is to provide an electric tooth-brush wherein the head portion and the grip portion can be separated through a simple operation but can be highly resistant against separation in the absence of the separation operation, and displacement of the head portion with respect to the grip portion can be prevented during use of the tooth-brush.

To accomplish this object, according to an embodiment of this invention, the head portion has a fork of two arms opposing the grip portion which are openable outwardly and normally have resilient tendency to inward closure, and the grip portion has, on its end surface opposing the arms, a boss which is fitted in a recess between the arms. Each arm is formed, at its tip, with a projection or a groove which is perpendicular to the axial direction of the handle, and the grip portion is formed, at its end surface opposing the fork and surrounding a base of the boss, with grooves or projections for snug reception of the projections or grooves of the two arms. For separation, the head portion and the grip portion are simply pulled in opposite directions. When these portions are coupled together, the fork normally having the resilient tendency to inward closure steadily clamps the boss of the grip portion to prevent easy separation of the two portions and additionally, the projections or grooves provided for the head portion perpendicularly to the axial direction of the handle snugly receive the grooves or projections provided for the end surface of the grip portion opposing the head portion so as to prevent relative rotational displacement of the two portions.

Still another object of this invention is to provide an electric tooth-brush wherein the usable term for the grip portion can be prolonged by preventing contact of the battery with water such as saliva which is responsible for reduction of lifetime of the battery.

To accomplish this object, according to another embodiment of the invention, the grip portion has, on its outer periphery near the head portion, a water blocking collar, and a resilient seal ring is interposed between the battery and the grip conductor member. The water blocking collar blocks a flow of water from the head portion to the grip portion and additionally, even a leakage flow of water is prevented by the resilient seal ring from intruding into the internal battery underlying the grip conductor member.

BRIEF DESCRIPTION OF THE DRAWINGS

In the accompanying drawings:

FIG. 1 is a plan view showing a grip portion and a head portion, illustrated as separated from each other, of an electric tooth-brush according to a first embodiment of the invention;

FIG. 2 is a rear view of the FIG. 1 embodiment after assembled;

DESCRIPTION OF THE PREFERRED EMBODIMENTS

Figure 3:
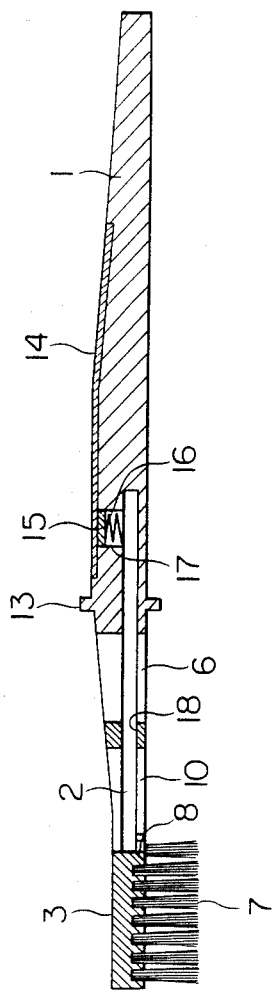
FIG. 3 is a longitudinal sectional view taken along line 3—3 in FIG. 2 and as viewed in a direction of arrow.

Referring to FIGS. 1 to 4, there is shown an electric tooth-brush according to a first embodiment of the invention. The electric tooth-brush has a handle comprised of a grip portion 1 and a head portion 3 removably coupled to the grip portion 1.

The grip portion 1 has, on its outer periphery of one end opposing the head portion 3, an annular, water blocking collar 13. A boss 5 having, on opposite sides of its tip, projections 12 extends from one end surface of the grip portion opposing the head portion. In the one end surface, there are formed grooves 19 each of which extends vertically in FIG. 1 and has a depth reaching the collar 13. A conductor bar 2 extends outwardly of the boss 5 and has a backward part which is inserted and fixed in the grip portion 1. The grip portion 1 is formed, near the backward end of the conductor bar 2, with a hole 17 which extends from an upper surface of the conductor bar 2 to a top surface of the grip portion 1. Within this hole 17, a spring 16 of a good electrically conductive material and a battery 15 are stacked sequentially from the conductor bar 2. The battery 15 has an upper positive pole and held in the hole 17 with its upper surface engaged with a metal cover plate 14 carried or mounted on the grip portion 1.

The head 3 has, at one end opposing the grip portion 1, a fork of two arms 4 between which there are formed a recess 9 substantially resembling the boss 5 for snug reception of the projections 12 and boss 5 and a slit 6 forwardly extending from a fore end of the recess 9 in the axial direction. Each of the arms 4 has, at its back end, a projection 11 which is snugly inserted in the groove 19. The head portion 3 has an axially extending communication hole 10 which is formed forwardly of the slit 6 and spaced therefrom. A fore, rear (bottom) end wall of the communication hole 10 is in communication with a plurality of small grooves 8 which extend sidewards and, in front of the small grooves 8, bristles 7 are studded in the rear (bottom) surface of the head portion. Formed in the head portion 3 is an insertion hole 18 for reception of the conductor bar 2, which insertion hole axially extends forwardly from the backward end of the head portion 3.

When brushing teeth with the tooth-brush of the above construction, a toothpaste containing fluoride is used. During brushing, the bristles 7 of the head portion 3 are wetted with saliva which in turn runs up along the bristles 7 and reaches, via the small grooves, the communication hole 10 in which the conductor bar 2 is wetted with the saliva. In this manner, the bristles 7 are electrically connected to the conductor bar 2 by the saliva and as a result, connected to a negative pole of the battery 15.

Since fingers of the user grasping the grip portion 1 are electrically connected to the positive pole of the battery 15 via the cover plate 14 under which, in this embodiment, the battery 15 is disposed, a closed circuit is established through the tooth-brush and the user body. Consequently, current from the battery 15 is passed to surfaces of teeth via the fingers and the dental pulp tissue and fluorine ions or negative ions conversely permeate from the surfaces of teeth into the teeth and precipitate therein to thereby strengthen quality of teeth and prevent tooth decay and pyorrhea. In use, the collar 13 blocks undesired saliva which would otherwise contaminate the fingers.

As the battery 15, a silver oxide battery having, for example, a diameter of 5.8 mm, a thickness of 1.65 mm, a voltage of 1.5 volts and a current capacity of 8 mAH is employed to provide a current of 20 to 30 $\mu$A which normally flows through the human body. Especially, when the body is wetted, a current of about 50 $\mu$A can be obtained. Thus, on the assumption that one tooth brushing is carried out for four minutes by holding the tooth-brush with wetted fingers, the aforementioned battery permits 2400 frequencies of tooth brushing. Accordingly, if tooth brushing is carried out twice a day, then the battery will serve for more than three years. Theoretically, the grip portion 1 can therefore serve by itself for the same period of time. On the contrary, the bristles 7 of the head portion 3 will be worn after used for about one month and will become of no use.

Figure 4:
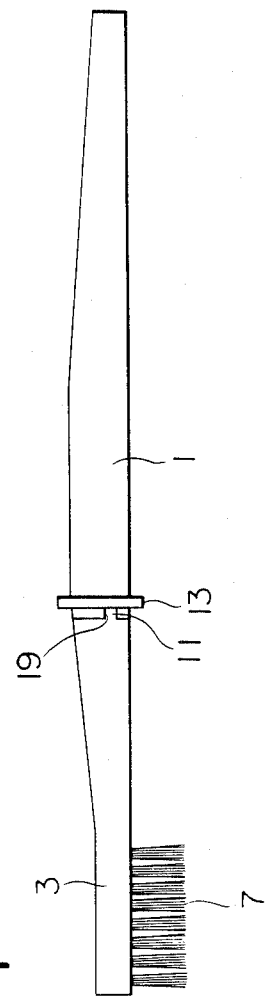
FIG. 4 is a front view of the FIG. 1 embodiment.
Figure 5:
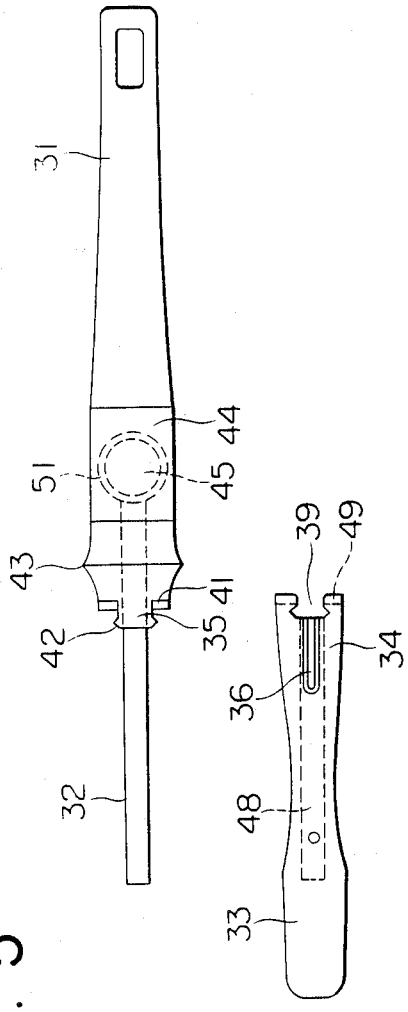
FIG. 5 is a plan view of an electric tooth-brush according to a second embodiment of the invention.
Figure 6:
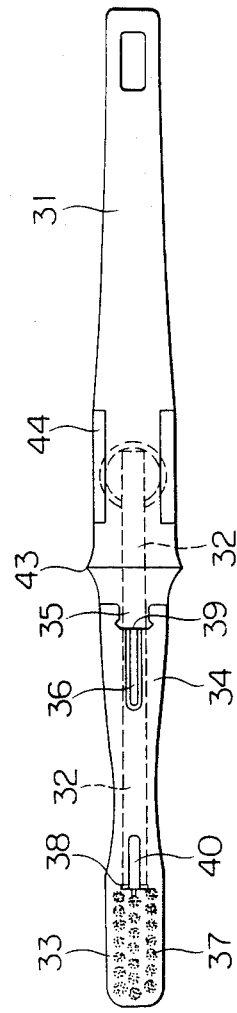
FIG. 6 is a rear view of the FIG. 5 embodiment.
Figure 7:
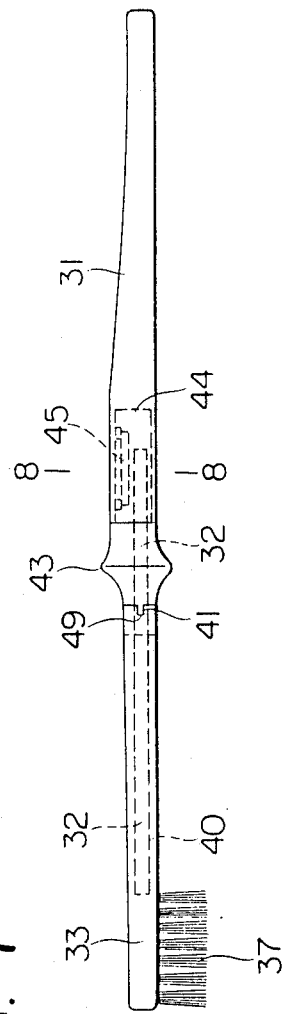
FIG. 7 is a front view of the FIG. 5 embodiment.
Figure 8:
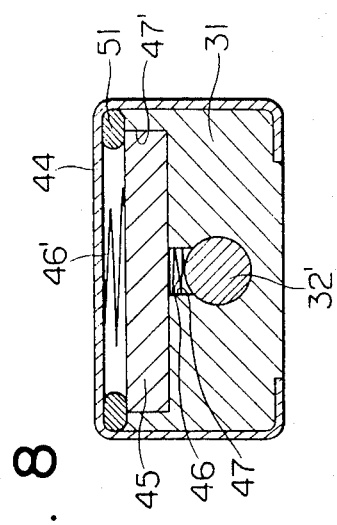
FIG. 8 is an enlarged crosssectional view taken along line 8—8 in FIG. 7.
Figure 9:
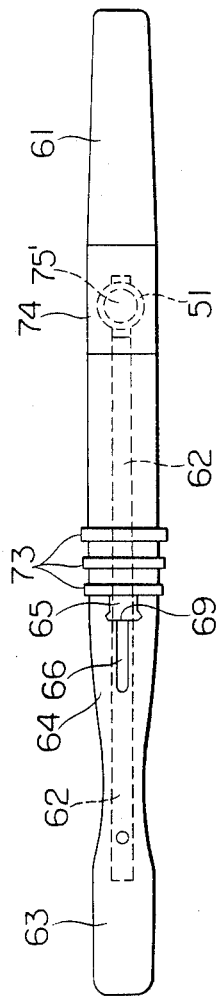
FIG. 9 is a plan view of an electric tooth-brush according to a third embodiment of the invention.
Figure 10:
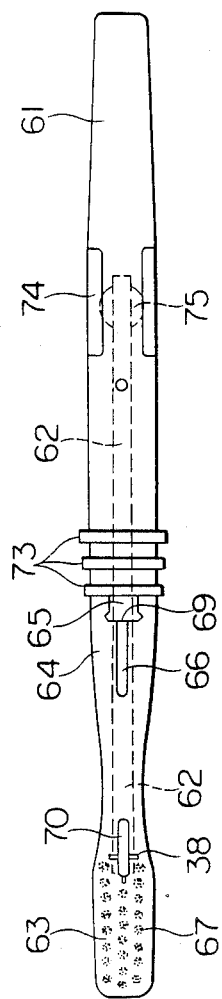
FIG. 10 is a rear view of the FIG. 9 embodiment.
Figure 11:
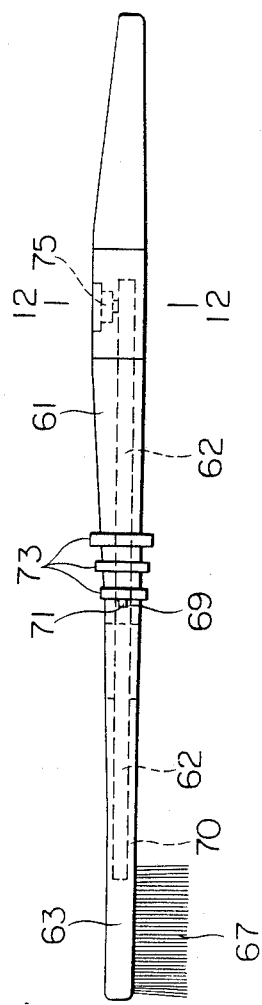
FIG. 11 is a front view of the FIG. 9 embodiment.
Figure 12:
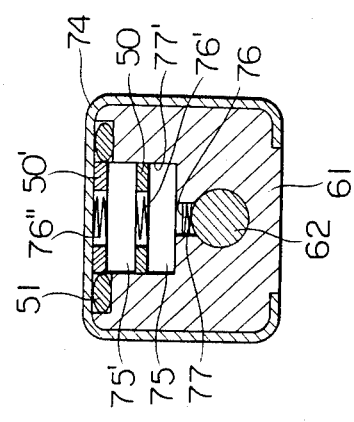
FIG. 12 is an enlarged crosssectional view taken along line 12—12 in FIG. 11.

In the previous embodiment, upon occurrence of wear of the bristles, the grip portion 1 is retained for use and only the head portion 3 is replaced with new one. In the handle assembled as shown in FIGS. 2 to 4, when the grip portion 1 and the head portion 3 are pulled in the opposite directions, the fork of arms 4 is opened to allow the boss to be pulled out of the recess 9 and the conductor bar 2 to be also pulled out of the insertion hole 18, with the result that the head portion 3 is separated from the grip portion 1 as shown in FIG. 1. To put together the two portions 1 and 3, the reverse operation is effected. When these portions 1 and 3 are coupled together, the projections 11 are fitted in the grooves 19 to ensure that one portion can be prevented from rotating with respect to the other portion. The conductor bar 2 is also effective to prevent the head portion 3 in use from deforming relative to the grip portion 1 in the vertical direction in FIG. 3. As will be seen from the foregoing, this embodiment provides an economical tooth-brush wherein one grip portion 1 can be retained several times for use with several head portions 3.

Referring to FIGS. 5 to 8, a second embodiment of the invention will be described. In these figures, reference numerals designating like members in FIGS. 1 to 4 illustrative of the first embodiment are added with thirty to designate like members in FIGS. 5 to 8 which will not be detailed herein. Other members will mainly be described in the following description.

In the second embodiment, a grip portion 31 is curved backwardly from a peak of a water blocking collar 43 to form a curved outer surface which fits for grasp by fingers. A cover plate 44 is fitted in a partial annular groove formed in the outer periphery of the grip portion 31 backwardly of the collar 43 and it automatically rests on the grip portion by its resiliency. A battery 45 is received in a large diameter hole 47'. The battery 45 is electrically connected to a conductor bar 32 by a spring 46 received in a small diameter hole 47 and to the cover plate 44 by a spring 46'. The battery 45 is held in place by means of a resilient seal ring 51 interposed between the upper peripheral edge of the battery 45 and the cover plate 44.

Since in this embodiment the cover plate 44 can be supported on the grip portion 31 without resort to any particular, independent fixtures but by its own resiliency, the tooth-brush can be simplified in construction and is easy to manufacture. In addition, the resilient seal ring 51 steadily prevents intrusive water between the grip portion 31 and the cover plate 44 from reaching the battery 45.

A third embodiment of the invention will now be described with reference to FIGS. 9 to 12 in a similar manner to the second embodiment by adding reference numerals designating like members of the first embodiment with sixty to designate like members of the third embodiment.

In the third embodiment, a grip portion 61 has a plurality of water blocking collars 73 whose heights are sequentially increased in proportion to distances from a head portion 63. As best seen from FIG. 12, a plurality of (two in this embodiment) batteries 75 and 75' are employed, and a spring 76 is interposed between a conductor bar 62 and the battery 75, a spring 76' between the batteries 75 and 75' and a spring 76" between the battery 75' and a cover plate 74. The spring 76 is received in a small diameter hole 77, and the batteries 75 and 75' are received in a large diameter hole 77'. The springs 76' and 76" are surrounded by annular insulating members 50 and 50', respectively. The annular insulating member 50' is also surrounded by a resilient seal ring 51 interposed between an upper surface of the grip portion 61 and a rear surface of the cover plate 74. This embodiment is different from the previous two embodiments in that projections 71 are provided for the grip portion 61 and grooves 79 are provided for a head portion 63.

If in the third embodiment the plurality of batteries 75 and 75' have each a capacity which is equal to the capacity of the battery 15 in the first embodiment, the total voltage becomes integer times (twice in this embodiment) the voltage of the battery 15. If the total voltage is desired to be equal to the voltage of the battery 15, the capacity of each of the batteries 75 and 75' becomes a fraction of integer of the capacity of the battery 15. In the third embodiment, however, the batteries 75 and 75' are connected in series and therefore, disigned differently from the battery 15 of the first embodiment. Consequently, the batteries 75 and 75' are insulated from each other by the insulating member 50 interposed therebetween, and the battery 75' is insulated from the cover plate 74 by the insulating member 50' interposed therebetween.

Additionally, the plurality of collars 73 in this embodiment enhance steady prevention of movement of saliva from the head portion 63 to the grip portion 61. Moreover, like the second embodiment, the resilient seal ring 51 fulfils sealing effect that steadily prevents intrusive water between the grip portion 61 and the cover plate 74 from reaching the batteries 75' and 75.

In the foregoing embodiments, the grip and head portions are typically molded from synthetic resin and the toothpaste containing fluoride is used upon use of the tooth-brush. But other kinds of toothpaste were used practically to confirm that a similar tendency to that by the toothpaste containing fluoride could be obtained.

Although a particular preferred embodiment of the invention has been disclosed in detail for illustrative purposes, it will be recognized that variations or modifications of the disclosed apparatus, including the rearrangement of parts, lie within the scope of the present invention.

What is claimed is:

1. An electric tooth-brush having a handle including a grip portion, and a head portion separable therefrom and studded with bristles, said head portion having a fork of two arms opposing said grip portion, which arms are openable outwardly and normally have a resilient tendency to inward closure, said grip portion having, on its end surface opposing said arms, a boss which is fitted in a recess between said arms, wherein said grip portion accommodates a battery and carries a head conductor member which has one end connected to one pole of said battery and the other end projecting outwardly from one end of said grip portion. opposing said head portion, and a grip conductor member which covers a top surface of said grip portion and which is connected to the other pole of said battery, and wherein said head portion is formed with an insertion hole in which said head conductor member is fitted and a fluid communication hole extending from said insertion hole to said bristles.

2. An electric tooth-brush according to claim 1 wherein each of said arms is formed, at its tip, with a projection of a groove which extends perpendicular to the axial direction of said handle, and said grip portion is formed, at its end surface opposing said fork and surrounding a base of said boss, with grooves or projections for snug reception of the projections or grooves, respectively, of said two arms.

3. An electric tooth-brush having a handle including a grip portion, a grip conductor member covering a top surface of said grip portion, and a head portion separable from said grip portion and studded with bristles, said grip portion carrying a head conductor member and having a vertical hole formed perpendicularly to said head conductor member, a battery received in said vertical hole, one pole of said battery being connected to said head conductor member by a spring and the other pole of said battery being engaged, by the urging force of said spring, to said grip conductor member, said head conductor member having one end projecting outwardly from one end of said grip portion opposing said head portion, said head portion being formed with an insertion hole in which said head conductor member is fitted and a fluid communication hole extending from said insertion hole to said bristles.

4. An electric tooth-brush according to claim 3 wherein said battery is connected to said grip conductor member by a spring.

5. An electric tooth-brush according to claim 4 wherein a resilient seal ring is interposed between said grip conductor member and said battery adjacent thereto.

6. An electric tooth-brush comprising a grip portion adapted to be gripped manually, an elongated head portion connected to and separable from said grip portion and studded with bristles, said head portion having an elongated lengthwise extending hole therein, a head conductor member projecting lengthwise from one end of said grip portion adjacent said head portion, slidably extending into said hole and terminating at a location within said hole which location is spaced from said bristles, at least part of the length of said head conductor member being covered by the wall that defines said hole, fluid communication passage means which extends from said bristles to said hole so that fluid can flow from said bristles to said head conductor member in said hole, a grip conductor member covering a surface of said grip portion, and an electric power source connected to said head conductor member and said grip conductor member.

7. An electric tooth-brush as set forth in claim 6, wherein said fluid communication passage means comprises a surface of said head portion on which said bristles are studded; and a passage extending from said surface of said head portion to said hole, whereby fluid flows from said bristles to said hole through said surface of said head portion.

8. An electric tooth-brush as set forth in claim 7, wherein said fluid communication passage means further comprises a groove provided on said surface of said head portion and extending substantially from said bristles to said passage for guiding fluid to flow from said bristles to said passage.

9. An electric tooth-brush as set forth in claim 7, wherein said head conductor member is a bar and said hole opens through the end of said head portion adjacent to said grip portion so as to receive said bar.

10. An electric tooth-brush as set forth in claim 9, wherein said passage comprises an opening on said surface of said head portion in communication with said hole.

11. An electric tooth-brush comprising a handle including a grip portion, a head portion consisting essentially of an electrically nonconductive material studded with brush bristles, mutually interengageable coupling means on both said grip portion and said head portion for releasably attaching said head portion to said grip portion, said grip portion comprising a battery compartment containing a battery and an elongated head conductor member which is in electrical connection with one pole of said battery and has one end extending outwardly from one end of said grip portion past said coupling means located on said handle, a grip conductor member disposed on a surface of said grip portion and in electrical connection with the other pole of said battery, said head portion being formed with a head conductor member receiving space which is adapted to receive said outwardly extending one end of said elongated head conductor member when said handle and said head portion are engaged, and a fluid communication path extending from said head conductor member receiving space to said brush bristles, said fluid communication path comprising the sole means for electrical connection between said brush bristles and said head conductor member.

12. The electric tooth-brush of claim 1 wherein said head portion consists essentially of an electrically nonconductive synthetic resin material studded with bristles.

13. The electric tooth-brush of claim 3 wherein said head portion consists essentially of an electrically nonconductive synthetic resin material studded with bristles.

14. The electric tooth-brush of claim 6 wherein said head portion consists essentially of an electrically nonconductive synthetic resin material studded with bristles.

15. An electric tooth-brush as claimed in claim 6 in which said head portion comprises an elongated shank extending away from said grip portion and an enlarged remote end portion on which said bristles are studded, said hole extending lengthwise through said shank, said head conductor member comprising a bar extending through said hole and terminating at a location close to and spaced from said bristles.

* * * * *